United States Patent
Ito et al.

(10) Patent No.: US 9,371,380 B2
(45) Date of Patent: Jun. 21, 2016

(54) ANTITUMOR AGENT AND THERAPEUTIC EFFECT PREDICTION METHOD FOR PATIENTS WITH KRAS-MUTATED COLORECTAL CANCER

(75) Inventors: Masanobu Ito, Tokyo (JP); Hiroyuki Okabe, Tsukuba (JP)

(73) Assignee: Taiho Pharmaceutical Co., Ltd., Tokyo (JP)

(*) Notice: Subject to any disclaimer, the term of this patent is extended or adjusted under 35 U.S.C. 154(b) by 18 days.

(21) Appl. No.: 14/238,569

(22) PCT Filed: Aug. 15, 2012

(86) PCT No.: PCT/JP2012/070745
§ 371 (c)(1),
(2), (4) Date: Feb. 12, 2014

(87) PCT Pub. No.: WO2013/024865
PCT Pub. Date: Feb. 21, 2013

(65) Prior Publication Data
US 2014/0213602 A1    Jul. 31, 2014

(30) Foreign Application Priority Data
Aug. 16, 2011 (JP) ................... 2011-177838

(51) Int. Cl.
*A61K 31/505* (2006.01)
*C07K 16/24* (2006.01)

(52) U.S. Cl.
CPC ........... *C07K 16/241* (2013.01); *C07K 2317/24* (2013.01); *C07K 2317/94* (2013.01)

(58) Field of Classification Search
CPC ........... C12Q 1/6886; C12Q 2600/106; C12Q 2600/156; A61K 31/513; A61K 31/7072
USPC ......................................... 514/274; 544/244
See application file for complete search history.

(56) References Cited

U.S. PATENT DOCUMENTS

| | | | |
|---|---|---|---|
| 7,799,783 B2 * | 9/2010 | Emura et al. ............... | 514/235.8 |
| 2006/0167031 A1 | 7/2006 | Emura | |

FOREIGN PATENT DOCUMENTS

| | | |
|---|---|---|
| CN | 101107001 A | 1/2008 |
| EP | 1849470 A1 | 10/2007 |
| RU | 2394581 C2 | 7/2010 |

OTHER PUBLICATIONS

Emura et al., "Potentiation of the antitumor activity of (alpha, alpha, alpha)-trifluorothymidine by the co-administration of an inhibitor of thymidine phosphorylase at a suitable molar ratio in vivo", Aug. 2005, International Journal of Oncology, vol. 27, No. 2, pp. 449-455.*

Overman et al, "Phase I Clinical Study of Three Times a Day Oral Administration of TAS-102 in Patients with Solid Tumors", Cancer Investigation, US, vol. 36, No. 8, Mar. 9, 2015, pp. 794-799, XP009182788, ISSN: 0735-7907, DOI: 10.1080/07357900802087242 the whole document.

European Search Report dated Mar. 9, 2015, for EP Application 12824342.5, 4 pages.

Irene V. Bijnsdorp et al., "Molecular mechanism underlying the synergistic interaction between trifluorothymidine and the epidermal growth factor receptor inhibitor erlotinib in human colorectal cancer cell lines", Cancer Science, 101:No. 2: pp. 440-447.

Godefridus J. Peters et al., "TAS-102: more than an antimetabolite", Lancet Oncology, vol. 13, e518-519.

Amado et al., "Wild-Type KRAS is Required for Panitumumab Efficacy in Patients with Metastatic Colorectal Cancer", Journal of Clinical Oncology, 2008, vol. 26, No. 10, pp. 1626-1634.

Baba et al., Phase II Study of Tas-102 in Patients with Metastatic Colorectal Cancer Refractory of Standard Chemotherapy (Differential Analysis of KRAS Status),The Journal of the Japan Society for Cancer Therapy, 2011, vol. 46, No. 2, p. 402, F04-5.

Hong et al., "Phase I Study to Determine the Safety and Pharmacokinetics of Oral Administration of TAS-102 in Patients with Solid Tumors", Cancer, 2006, vol. 107, No. 6, pp. 1383-1390.

Karapetis et al., "K-ras Mutations and Benefit from Cetuximab in Advanced Colorectal Cancer", The New England Journal of Medicine, 2008, vol. 359, No. 17, pp. 1757-1765.

Kuboki et al, "6005 Oral a Multicenter, Randomized, Double-blind, Phase II Study of TAS-102(A) . . . ", European Journal of Cancer, 2011, vol. 47, supplement 1, p. S392, 6005.

Yamazaki et al., "A multicenter, randomized, double-blind, phase II study of TAS-102 plus best supportive care (BSC) (A) versus placebo plus . . . ", The 9th Annual Meeting of Japanese Society of Medical Oncology, Program Shorokushu, 2011, p. 170, PL-1.

NCCN Clinical Practice Guidelines in Oncology (NCCN Guidelines TM), Colon Cancer (Version 3.2011), 2011, 94 pages.

NCCN Clinical Practice Guidelines in Oncology (NCCN Guidelines TM), Rectal Cancer (Version 4.2011), 2011, 80 pages.

Office Action dated Feb. 24, 2015 in Russian Application No. 2014109999, 8 pages.

* cited by examiner

*Primary Examiner* — My-Chau T Tran
(74) *Attorney, Agent, or Firm* — Rothwell, Figg, Ernst & Manbeck, P.C.

(57) ABSTRACT

This invention provides a method for predicting a therapeutic effect of chemotherapy that uses an antitumor agent comprising α,α,α-trifluorothymidine and 5-chloro-6-(1-(2-iminopyrrolidinyl)methyl)uracil hydrochloride at a molar ratio of 1:0.5 on a colorectal cancer patient,
the method comprising:
(1) detecting the presence or absence of KRAS gene mutation in a biological sample obtained from the patient; and
(2) predicting that the patient is likely to sufficiently respond to the chemotherapy, when KRAS gene mutation is detected in Step (1).

3 Claims, 2 Drawing Sheets

ANTITUMOR AGENT AND THERAPEUTIC EFFECT PREDICTION METHOD FOR PATIENTS WITH KRAS-MUTATED COLORECTAL CANCER

CROSS REFERENCE TO RELATED APPLICATION

This application is a 35 U.S.C. 371 National Phase Entry Application from PCT/JP2012/070745, filed Aug. 15, 2012, which claims the benefit of Japanese Patent Application No. 2011-177838 filed on Aug. 16, 2011, the disclosure of which is incorporated herein in its entirety by reference.

TECHNICAL FIELD

The present invention relates to a method for predicting a therapeutic effect of chemotherapy that uses an antitumor agent (hereinafter referred to as TAS-102) containing $\alpha,\alpha,\alpha$-trifluorothymidine (FTD) and 5-chloro-6-(1-(2-iminopyrrolidinyl)methyl)uracil hydrochloride (TPI) at a molar ratio of 1:0.5, and also relates to an antitumor agent to be administered to a patient who is predicted to sufficiently respond to the chemotherapy using the antitumor agent.

BACKGROUND ART

The standard therapy for treating colorectal cancer patients has been performed, typically, with chemotherapy using fluoropyrimidine-based antitumor agent (e.g., a combination of 5-fluorouracil (5-FU) and leucovorin (LV)), and optionally, with multidrug chemotherapy (FOLFIRI, FOLFOX, or the like) that additionally uses irinotecan or oxaliplatin. Such methods have achieved a certain therapeutic effect (Non-Patent Document 1).

However, when a colorectal cancer patient becomes refractory or intolerant to these standard therapies using 5-FU, irinotecan, or oxaliplatin, the choice of antitumor agent that can significantly prolong their survival is very limited. Further, although cetuximab, which is a chimeric antibody targeting the epithelial growth factor receptor (EGFR), and panitumumab, which is a fully human monoclonal antibody, are often selected for such colorectal cancer patients who are refractory or intolerant to standard therapy, it has been reported that these antitumor agents had no effects when the patients have colorectal cancer with KRAS gene mutation (Non-Patent Documents 2 and 3).

As explained above, despite the vigorous development of chemotherapies for colorectal cancer patients, their therapeutic effects are still insufficient. In particular, effective chemotherapies have not substantially been established for colorectal cancer patients with KRAS gene mutation. Further, since the effects of chemotherapies greatly depend on the genetic factors of the patients, there is no way to estimate the effects of the antitumor agents before the actual administration.

CITATION LIST

Non-Patent Documents

Non-Patent Document: NCCN Clinical Practice Guidelines in Oncology (NCCN Guidelines™); Colon Cancer (Version 3, 2011), Rectal Cancer (Version 4, 2011)
Non-Patent Document 2: N Engl J Med. 2008; 359 (17): 1757-65.
Non-Patent Document 3: J Clin Oncol. 2008; 26 (10): 1626-34.

SUMMARY OF INVENTION

Technical Problem

An object of the present invention is to provide chemotherapy for colorectal cancer patients that ensure a significant survival-prolongation effect and fewer side effects.

Solution to Problem

The present inventors conducted extensive research on various chemotherapies for colorectal cancer patients, and found that colorectal cancer patients with KRAS gene mutation are more likely to respond to TAS-102 than wild-type patients; and that, therefore, it becomes possible to estimate the adequacy of the therapeutic effect of chemotherapy using TAS-102 on a patient by detecting the presence/absence of KRAS gene mutation as an indicator. Based on this finding, the inventor completed the present invention.

Specifically, the present invention provides the following methods and antitumor agents.

Item 1. A method for predicting a therapeutic effect of chemotherapy that uses an antitumor agent comprising $\alpha,\alpha,\alpha$-trifluorothymidine and 5-chloro-6-(1-(2-iminopyrrolidinyl)methyl)uracil hydrochloride at a molar ratio of 1:0.5 on a colorectal cancer patient,
the method comprising the steps of:
(1) detecting the presence or absence of KRAS gene mutation in a biological sample obtained from the patient; and
(2) predicting that the patient is likely to sufficiently respond to the chemotherapy, when KRAS gene mutation is detected in Step (1).

Item 2. The method according to Item 1, wherein the KRAS gene mutation is a mutation of codon 12 and/or codon 13.

Item 3. The method according to Item 1 or 2, wherein the colorectal cancer patient is a colorectal cancer patient who is refractory or intolerant to standard therapy.

Item 4. An antitumor agent comprising $\alpha,\alpha,\alpha$-trifluorothymidine and 5-chloro-6-(1-(2-iminopyrrolidinyl)methyl)uracil hydrochloride at a molar ratio of 1:0.5 for use in the treatment of a colorectal cancer patient, who is assumed to sufficiently respond to chemotherapy that uses an antitumor agent comprising $\alpha,\alpha,\alpha$-trifluorothymidine and 5-chloro-6-(1-(2-iminopyrrolidinyl)methyl)uracil hydrochloride at a molar ratio of 1:0.5, according to the methods of Items 1 to 3.

Item 5. A method for treating colorectal cancer, comprising performing chemotherapy using an antitumor agent comprising $\alpha,\alpha,\alpha$-trifluorothymidine and 5-chloro-6-(1-(2-iminopyrrolidinyl)methyl)uracil hydrochloride at a molar ratio of 1:0.5 on a colorectal cancer patient, who is assumed to sufficiently respond to chemotherapy that uses an antitumor agent comprising $\alpha,\alpha,\alpha$-trifluorothymidine and 5-chloro-6-(1-(2-iminopyrrolidinyl)methyl)uracil hydrochloride at a molar ratio of 1:0.5, according to the methods of Items 1 to 3.

Item 6. Use of an antitumor agent comprising $\alpha,\alpha,\alpha$-trifluorothymidine and 5-chloro-6-(1-(2-iminopyrrolidinyl)methyl)uracil hydrochloride at a molar ratio of 1:0.5 for performing treatment of a colorectal cancer patient, who is assumed to sufficiently respond to chemotherapy that uses an antitumor agent comprising $\alpha,\alpha,\alpha$-trifluorothymidine and 5-chloro-6-(1-(2-iminopyrrolidinyl)methyl)uracil hydrochloride at a molar ratio of 1:0.5, according to the methods of Items 1 to 3.

Item 7. An antitumor agent for treating a colorectal cancer patient with KRAS gene mutation, the antitumor agent comprising α,α,α-trifluorothymidine and 5-chloro-6-(1-(2-iminopyrrolidinyl)methyl)uracil hydrochloride at a molar ratio of 1:0.5.

Item 8. A method for treating colorectal cancer, comprising performing chemotherapy that uses an antitumor agent comprising α,α,α-trifluorothymidine and 5-chloro-6-(1-(2-iminopyrrolidinyl)methyl)uracil hydrochloride at a molar ratio of 1:0.5 on a colorectal cancer patient with KRAS gene mutation.

Item 9. Use of an antitumor agent comprising α,α,α-trifluorothymidine and 5-chloro-6-(1-(2-iminopyrrolidinyl)methyl)uracil hydrochloride at a molar ratio of 1:0.5 for treating a colorectal cancer patient with KRAS gene mutation.

Advantageous Effects of Invention

By using the prediction method of the present invention, it becomes possible to provide chemotherapy that ensures more significant survival-prolongation effects with respect to colorectal cancer patients (in particular, with respect to colorectal cancer patients who are refractory or intolerant to standard therapy, i.e., patients that antitumor agents had little effect on, and thus those that had few choices regarding antitumor agents for significantly prolonging their survival).

In addition, although it has been reported that TAS-102 has a therapeutic effect on solid cancers including colorectal cancers (Cancer Invest. 2008; 26(8):794-9.), the superior therapeutic effect of TAS-102, particularly on KRAS gene mutation-type colorectal cancer patients, has not been recognized. Moreover, since it was known that the survival of KRAS gene mutation-type colorectal cancer patients is shorter than that of wild-type colorectal cancer patients, the significant survival-prolongation effect of TAS-102 on the KRAS gene mutation-type colorectal cancer patients is an unexpected effect.

DESCRIPTION OF EMBODIMENTS

Figure 1:
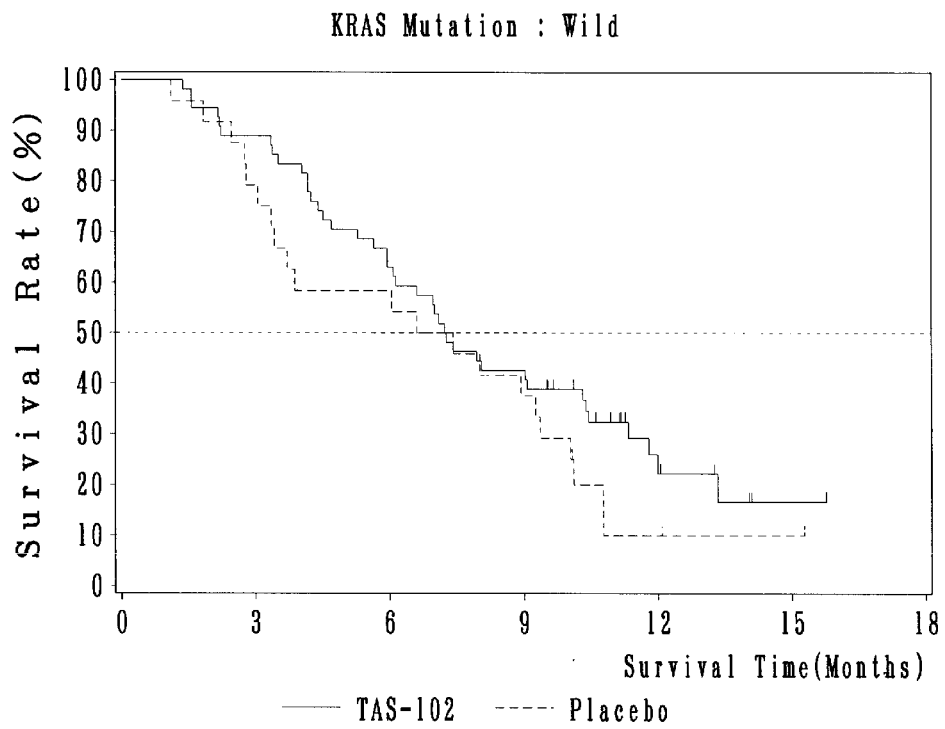
FIG. 1 shows Kaplan-Meier survival curves of KRAS gene wild-type patients.

The prediction method of the present invention predicts whether chemotherapy using TAS-102 has a sufficient therapeutic effect on a colorectal cancer patient, based on the presence or absence of KRAS gene mutation in the patient.

The protein of KRAS gene, which is used as an indicator in the present invention, is a type of G protein having a molecular weight of 21,000 localized inside the cell membrane, and that is known to be involved in cell proliferation by transmitting epidermal growth factor signals to the nucleus. In addition, there are reports that mutation of codon 12 and/or 13 in KRAS gene causes persistent transmission of EGFR signals.

The target patients of the present invention are colorectal cancer patients. In the present invention, "colorectal cancer" refers to a malignant tumor generated in colon or rectum, including primary colorectal cancers, locally recurrent colorectal cancers, and metastatic colorectal cancers that have spread to other tissue (e.g., liver). The "colorectal cancer patients" include not only patients currently having colorectal cancer tumor tissues, but also patients who have undergone resection of colorectal cancer tumor tissues. Therefore, in this specification, the therapeutic effect of chemotherapy encompasses shrinkage of colorectal cancers, suppression of proliferation, survival prolongation, as well as suppression of recurrence of colorectal cancers after resection of tumor tissues.

Further, the treatment history of the colorectal cancer patients of the present invention is not particularly limited insofar as the patients can endure administration of TAS-102; however, the target patients are preferably colorectal cancer patients who are refractory or intolerant to standard therapy, in terms of prediction accuracy of the present invention. In the present invention, "standard therapy" refers to chemotherapy that uses a fluoropyrimidine-based antitumor agent (e.g., a combination of 5-fluorouracil (5-FU) and leucovorin (LV)) or combination chemotherapy (FOLFIRI, FOLFOX, or the like) that uses irinotecan or oxaliplatin, in addition to the fluoropyrimidine-based antitumor agent. Herein, the condition "refractory or intolerant to standard therapy" refers to a state in which the patient is not responsive to the standard therapy (including the cases where progression (PD) is observed during the standard therapy, the cases where cancer recurrence is found during or within 6 months after the standard therapy conducted as postoperative adjuvant chemotherapy, and the like), a state in which the patient is unable to withstand the administration of a standard amount of the antitumor agent due to aggravation of disease or side effects, or the like.

In the present invention, "TAS-102" refers to an antitumor agent containing α,α,α-trifluorothymidine and 5-chloro-6-(1-(2-iminopyrrolidinyl)methyl)uracil hydrochloride at a molar ratio of 1:0.5. The antitumor agent is known for its antitumor effect mainly on solid cancers, such as colorectal cancers, through oral administration (pamphlet of WO96/30346).

"α,α,α-trifluorothymidine" is a known nucleic acid derivative in which a methyl group at 5-position of thymidine is substituted with a trifluoromethyl group, and is known for its antitumor effect due to DNA synthesis inhibitory activity (J. Am. Chem. Soc. 84:3597-3598, 1962; J. Med. Chem., 7:1-5, 1964; Biochemistry, 33:15086-15094, 1994).

"5-chloro-6-(1-(2-iminopyrrolidinyl)methyl)uracil hydrochloride" is a known compound having an activity for inhibiting thymidine phosphorylase activity, and is known for its effect of enhancing an antitumor effect (pamphlet of WO96/30346), metastasis inhibition effect (pamphlet of WO98/13045), effect of alleviating gastrointestinal side effects of antitumor agents (pamphlet of WO00/56337), anti-HIV effect (pamphlet of WO01/34162), effect of enhancing radial ray treatment (pamphlet of WO2008/001502), and therapeutic effect on inflammatory bowel disease (pamphlet of WO2009/047904).

TAS-102 may be provided as a combination drug (a preparation containing a plurality of active ingredients) obtained by formulating α,α,α-trifluorothymidine and 5-chloro-6-(1-(2-iminopyrrolidinyl)methyl)uracil hydrochloride into a single dosage form (single-formulation type), or may be provided as single active ingredient preparations by formulating each of the active ingredients into a plurality of dosage forms. Of these, a combination drug of α,α,α-trifluorothymidine and 5-chloro-6-(1-(2-iminopyrrolidinyl)methyl)uracil hydrochloride is preferable.

The dosage form of the antitumor agents is not particularly limited, and can be suitably selected depending on the purpose of the treatment. Specific examples thereof include oral preparations (such as tablets, coated tablets, powders, granules, capsules, and fluids), injections, suppositories, patches, and ointments. Of these, the combination drug containing α,α,α-trifluorothymidine and 5-chloro-6-(1-(2-iminopyrrolidinyl)methyl)uracil hydrochloride is preferably in the form of an oral preparation. Each antitumor agent can be prepared by a commonly known method, using one or more pharmacologically acceptable carriers in accordance with each dosage form. Examples of the carriers include those that are widely used in common drugs, such as excipients, binders, disintegrators, lubricants, diluents, solubilizing agents, suspending agents, tonicity adjusting agents, pH adjusters, buffers, stabilizers, colorants, sweetening agents, and flavoring agents.

"Chemotherapy in which an antitumor agent containing α,α,α-trifluorothymidine and 5-chloro-6-(1-(2-iminopyrrolidinyl)methyl)uracil hydrochloride at a molar ratio of 1:0.5" refers to chemotherapy in which at least TAS-102 is administered; this includes chemotherapy using TAS-102 alone, and chemotherapy using TAS-102 and other antitumor agents.

The administration schedule of the chemotherapy is suitably selected according to conditions such as the patient's age, sex, stage of disease, presence or absence of metastasis, and history of treatment. For example, it is preferable to repeat the following 4-week administration course. In each course, TAS-102 is administered from Day 1 to Day 5, and from Day 8 to Day 12, 2 to 4 times a day in an FTD (α,α,α-trifluorothymidine) amount of 20 to 80 mg/m$^2$ (per body surface area)/day, preferably 2 to 3 times a day in an FTD amount of 50 to 70 mg/m$^2$ (per body surface area)/day, more preferably 2 times a day in an FTD amount of 70 mg/m$^2$ (per body surface area)/day.

The chemotherapy of the present invention may be preoperative adjuvant chemotherapy in which the chemotherapy is performed before resection of tumor, or postoperative adjuvant chemotherapy in which the chemotherapy is performed after resection of tumor.

In the present invention, "therapeutic effect" can be evaluated based on a tumor-shrinking effect, an effect of suppressing recurrence, an effect of prolonging survival, etc. The effect of suppressing recurrence can be represented by extension of progression-free survival or the degree of improvement in recurrence rate. "Survival" can be represented by the degree of extension of the median of overall survival or progression-free survival. "Sufficiently respond to chemotherapy using an antitumor agent containing α,α,α-trifluorothymidine and 5-chloro-6-(1-(2-iminopyrrolidinyl) methyl)uracil hydrochloride at a molar ratio of 1:0.5" means a superior therapeutic effect by the administration of TAS-102, including a significant extension of survival, and a significant suppression of recurrence, compared with a treatment without the administration of TAS-102.

The prediction method of the present invention comprises Steps (1) and (2) described below.

Step (1) is a step of detecting the presence or absence of KRAS gene mutation in a biological sample obtained from a patient.

The biological sample is not particularly limited, as long as it is obtained from a cancer patient and contains cancer cells. Examples thereof include body fluid (such as blood and urine), tissue, extracts thereof, and cultures of obtained tissue. The method for obtaining the biological sample can be suitably selected according to the type of biological sample.

In the present invention, examples of "KRAS gene mutation" include mutations of codons 12, 13, and 61. In terms of accuracy in the prediction of the present invention, the mutations of codons 12 and 13 are preferable. More specifically, examples includes a mutation in which glycine of codon 12 is converted to serine, aspartic acid, valine, cysteine, alanine or arginine due to point mutation of the first or second base of codon 12 of KRAS gene, and a mutation in which glycine of codon 13 is converted to aspartic acid due to point mutation of the second base of codon 13 of KRAS gene (Clin Cancer Res. 17(14):4901-4914, 2011; J Mol Diagn. 12(1):43-50, 2010).

The method for detecting KRAS gene mutation of the present invention is not particularly limited insofar as the above mutations can be found, and a known detection method can be used. Examples of detection methods include the direct sequence method, and the Scorpion-ARMS method (RT-PCR) (Nature Biotech 17:804-807, 1999). The Scorpion-ARMS method is preferable in terms of the detection sensitivity. Further, commercially available detection kits, such as TheraScreen: KRAS (produced by DxS Limited may be used.

The biological sample is prepared through suitable treatment according to these measurement methods. Further, the reagents containing one or more primers or probes used for the detection may be prepared through a common method according to these measurement methods.

Step (2) is a step of predicting that the patient is likely to sufficiently respond to chemotherapy that uses TAS-102, when KRAS gene mutation is detected in Step (1).

EXAMPLES

Examples are given below to illustrate the present invention in more detail. Needless to say, the present invention is not limited to these Examples.

Example 1

Progressive recurring colorectal cancer patients (169 cases) who are refractory or intolerant to standard therapy including 5-FU, irinotecan, and oxaliplatin, and who have a treatment history of at least 2 regimens, are divided into a TAS-102 administration group (112 cases) and a placebo group (57 cases). There was no significant background difference between these two groups (including percentage of male patients (TAS-102 administration group, 57.1%; placebo group, 49.1%), average age (TAS-102 administration group, 63; placebo group, 62), ECOG PS 0 (TAS-102 administration group, 64.3%; placebo group, 61.4%), and percentage of the patients having a treatment history of 3 or more regimens (TAS-102 administration group, 84.8%; placebo group, 77.2%)). In the TAS-102 administration group, during the 4-week administration course, TAS-102 was administered twice a day in an FTD amount of 70 mg/m$^2$ (per body surface area) /day from Day 1 to Day 5 and from Day 8 to Day 12. This administration schedule was regarded as one course, and the course was repeatedly performed. On the other hand, no antitumor agent, including TAS-102, was given to the placebo group.

The overall survival (OS) was evaluated in all cases. Further, lesional tissues were obtained from 149 cases (TAS-102 administration group: 99 cases, placebo group: 50 cases) out of all cases, and the presence or absence of the mutation of codons 12 and 13 of KRAS gene was detected according to the Scorpion-Arms method using TheraScreen: KRAS (DxS Limited).

Figure 2:
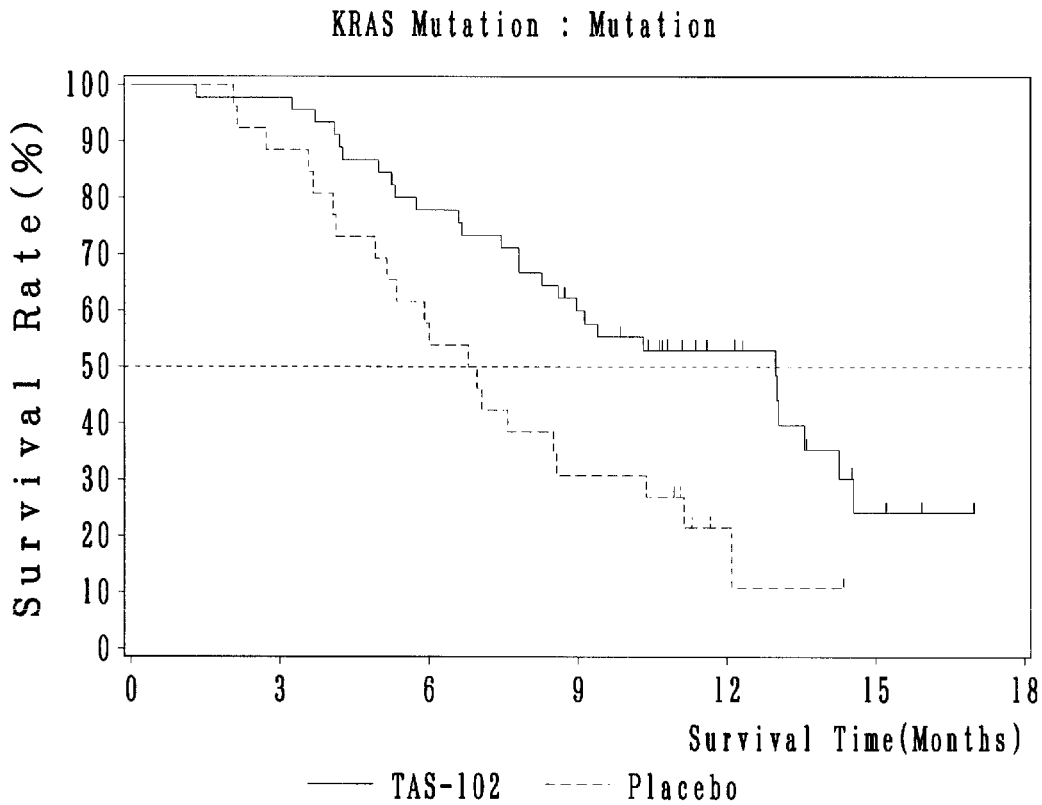
FIG. 2 shows Kaplan-Meier survival curves of KRAS gene mutation-type patients.

The relationship between the overall survival and the KRAS gene mutation was analyzed in the TAS-102 administration group and the placebo group. Table 1 shows the results. Further, FIGS. 1 and 2 show survival curves of KRAS mutation-type and wild-type according to the Kaplan-Meier method.

TABLE 1

| Patients | Group * | N | Median OS (months) | HR | 95% CI | P value |
|---|---|---|---|---|---|---|
| All | A | 112 | 9.0 | 0.56 | [0.39, 0.81] | 0.0011 |
|  | P | 57 | 6.6 |  |  |  |
| wt | A | 54 | 7.2 | 0.70 | [0.41, 1.20] | 0.191 |
|  | P | 24 | 7.0 |  |  |  |
| mt | A | 45 | 13.0 | 0.44 | [0.25, 0.80] | 0.006 |
|  | P | 26 | 6.9 |  |  |  |

* Group; A (TAS-102 Administration Group), P (Placebo Group) HR (Hazard Ratio), 95% CI (95% Confidence Interval), wt (absence of mutation of codons 12 and 13) mt (presence of mutation of codons 12 and/or 13)

Among the patients with KRAS gene mutation, the median (13.0 months) of the overall survival in the TAS-102 administration group is statistically significantly long compared with that of the placebo group (6.9 months). This confirms the unprecedented superior survival-prolongation effect of TAS-102 on the patients with KRAS gene mutation (HR=0.44, [95% CI: 0.25-0.80], p=0.006).

It is known that the patients with KRAS gene mutation generally have a shorter survival than the wild-type patients. However, the survival-prolongation effect of TAS-102 is greater in the patients with KRAS mutation than in the patients with wild-type KRAS (mutation-type: 13.0 months, wild-type: 7.2 months). Such an effect is unexpected to a person skilled in the art.

In an experiment with regard to all cases, i.e., all cases regardless of the type of KRAS gene, the median of the overall survival of the TAS-102 administration group was also significantly statistically long (9.0 months) compared with the placebo group (6.6 months), thus confirming that TAS-102 provides a superior survival-prolongation effect to progressive recurring colorectal cancer patients who are refractory or intolerant to standard therapy (HR=0.56, [95% CI: 0.39-0.81], p=0.0011).

Example 2

Next, in order to verify the usability of TAS-102 with respect to the KRAS gene mutation-type colorectal cancer patients, an in vivo efficacy test was performed in a nude mouse subcutaneously transplanted with a human colorectal cancer strain.

TAS-102 was orally administered to nude mice transplanted with human colorectal cancer strain HCT-116, which is known as a KRAS mutation-type, twice a day for 14 consecutive days in an FTD amount of 150 mg/kg/day by an ordinary method (TAS-102 Administration Group). Further, as a comparative group, cetuximab, which is often clinically used for colorectal cancer patients who are refractory or intolerant to standard therapy including 5-FU, irinotecan, and oxaliplatin, was intraperitoneally administered in an amount of 40 mg/kg/day on Day 1, Day 5, Day 8, and Day 12 (this administration amount is confirmed for the antitumor effect in other cancers). In contrast, no drug was administered in the control group. The antitumor effect was evaluated in each of these administration groups.

The major axis and the minor axis of each tumor were measured twice a week with a digital vernier caliper to find the tumor volume (TV). At the same time, the body weights were measured as an indicator of side effects. According to the tumor volumes thus obtained, a relative tumor volume (RTV) and a tumor growth inhibition rate (IR) were calculated according to the following equations.

$$RTV_n = (TV \text{ on Day } n)/(TV \text{ on Day } 0)$$

$$IR(\%) = [1-(\text{average } RTV_n \text{ value in the drug administration group})/(\text{average } RTV_n \text{ value in the control group})] \times 100$$

Figure 3:
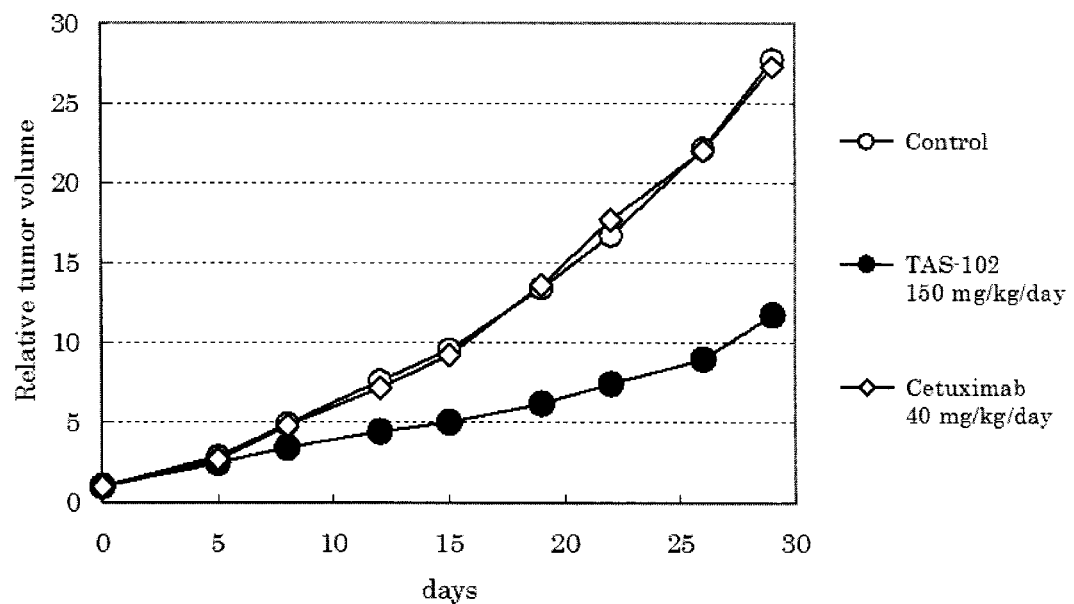
FIG. 3 is a graph showing relative tumor volumes of several nude mice groups implanted with a colorectal cancer strain and administered with different agents.
TAS-102: p.o., Days 1-14 (b.i.d.)
Cetuximab: i.p., Days 1, 5, 8, 12

FIG. 3 shows the results. The tumor growth inhibition rate on the final measurement day (Day 29) for the TAS-102 administration group was 57.7%, showing a statistically significant antitumor effect. On the other hand, the tumor growth inhibition rate in the cetuximab administration group was 1.7%; the antitumor effect was not substantially exhibited. Further, in all groups, severe weight loss was not observed.

Accordingly, it was proved that TAS-102 is clinically useful for the colorectal cancer patients regardless of the presence/absence of KRAS gene mutation, and that such a therapeutic effect of TAS-102 is particularly significant for patients with KRAS gene mutation.

The invention claimed is:
1. A method for treating a colorectal cancer patient, the method comprising the steps of:
    (1) detecting the presence or absence of a KRAS gene mutation in a biological sample obtained from the patient;
    (2) determining that the patient is likely to respond to a chemotherapy that uses an antitumor agent comprising α,α,α-trifluorothymidine and 5-chloro-6-(1-(2-iminopyrrolidinyl)methyl)uracil hydrochloride at a molar ratio of 1:0.5, when the KRAS gene mutation is detected in Step (1); and
    (3) performing the chemotherapy using said antitumor agent on the patient, when the patient is determined to likely respond to the chemotherapy in Step (2).
2. The method according to claim 1, wherein the KRAS gene mutation is a mutation of codon 12 and/or codon 13.
3. The method according to claim 1, wherein the colorectal cancer patient is a colorectal cancer patient who is refractory or intolerant to standard therapy.

* * * * *